US00PP34147P2

(12) United States Plant Patent
Mellema

(10) Patent No.: US PP34,147 P2
(45) Date of Patent: Apr. 19, 2022

(54) ***ALLIUM* PLANT NAMED 'IFALCOD'**

(50) Latin Name: *Allium tuberosum*
Varietal Denomination: IFALCOD

(71) Applicant: INNOFLORA PLANT BREEDING B.V., Heerhugowaard (NL)

(72) Inventor: Wietse Mellema, Creil (NL)

(73) Assignee: INNOFLORA PLANT BREEDING B.V., Heerhugowaard (NL)

( * ) Notice: Subject to any disclaimer, the term of this patent is extended or adjusted under 35 U.S.C. 154(b) by 0 days.

(21) Appl. No.: 17/459,910

(22) Filed: Aug. 27, 2021

(51) Int. Cl.
*A01H 5/02* (2018.01)
*A01H 6/04* (2018.01)

(52) U.S. Cl.
USPC ..... Plt./263.1
CPC ..... *A01H 6/045* (2018.05)

(58) Field of Classification Search
USPC ..... Plt./263.1
CPC ..... A01H 6/045; A01H 5/02
See application file for complete search history.

*Primary Examiner* — Keith O. Robinson
(74) *Attorney, Agent, or Firm* — C. Anne Whealy

(57) ABSTRACT

A new and distinct cultivar of *Allium* plant named 'IFALCOD', characterized by its upright plant habit with upright flowering stems; moderately vigorous to vigorous growth habit and moderately rapid growth rate; ensiform medium green-colored leaves; early and freely flowering habit; numerous white-colored flowers arranged on dense inflorescences; long flowering period; and good garden performance.

2 Drawing Sheets

Figure 1:
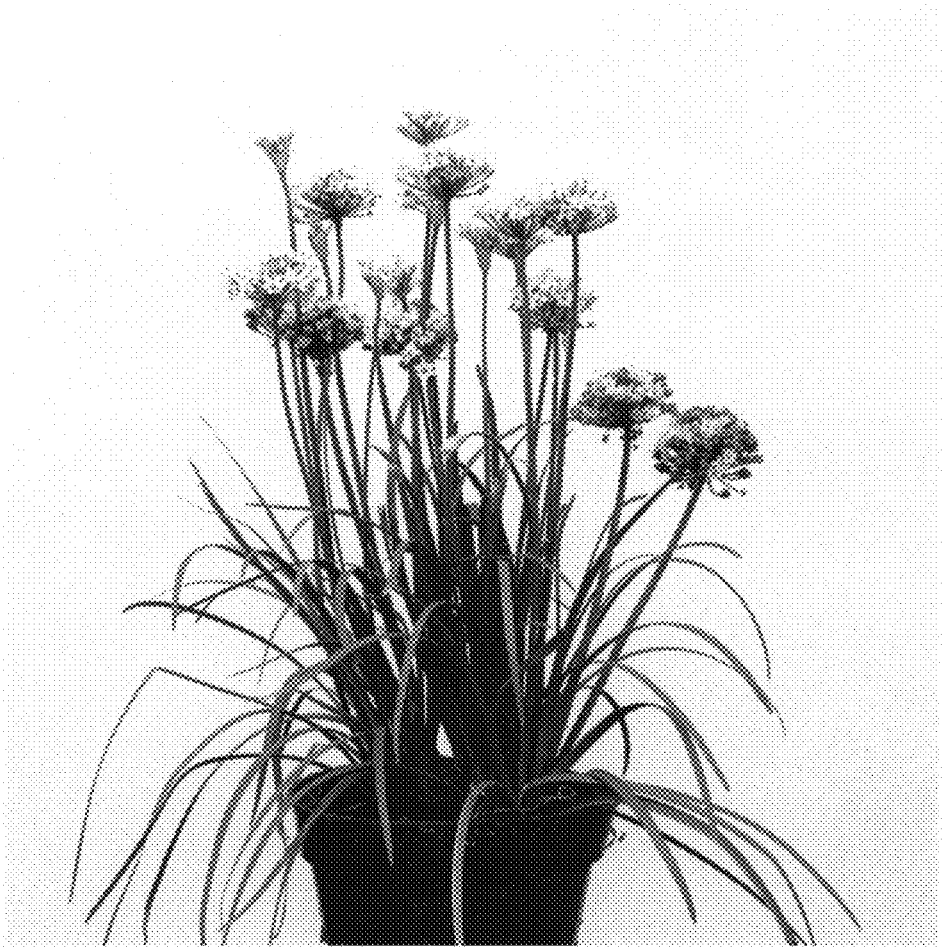

Botanical designation: *Allium tuberosum.*
Cultivar denomination: 'IFALCOD'.

PLANT BREEDER'S RIGHTS APPLICATION INFORMATION

An European Community Plant Breeder's Rights application for the instant plant was filed by the Applicant/Assignee, Innoflora Plant Breeding B.V. of Heerhugowaard, The Netherlands on Aug. 31, 2020, application number 2020/2058. Foreign priority is not claimed to this application.

BACKGROUND OF THE INVENTION

The present invention relates to a new and distinct cultivar of *Allium* plant, botanically known as *Allium tuberosum* and hereinafter referred to by the name 'IFALCOD'.

The new *Allium* plant is a product of a planned breeding program conducted by the Inventor in Heerhugowaard, The Netherlands. The objective of the breeding program is to create new compact and freely-flowering *Allium* plants with attractive flowers and good container and garden performance.

The new *Allium* plant originated from an open-pollination in May, 2007 of an unnamed selection of *Allium tuberosum*, not patented, as the female, or seed, parent with an unknown selection of *Allium tuberosum* as the male, or pollen, parent. The new *Allium* plant was discovered and selected by the Inventor as a single flowering plant from within the progeny of the stated open-pollination grown in a controlled greenhouse environment in Heerhugowaard, The Netherlands in 2010.

Asexual reproduction of the new *Allium* plant by divisions in a controlled environment in Heerhugowaard, The Netherlands since 2011 has shown that the unique features of this new *Allium* plant are stable and reproduced true to type in successive generations.

SUMMARY OF THE INVENTION

Plants of the new *Allium* have not been observed under all possible combinations of environmental conditions and cultural practices. The phenotype may vary somewhat with variations in environmental conditions such as temperature and light intensity without, however, any variance in genotype.

The following traits have been repeatedly observed and are determined to be the unique characteristics of 'IFALCOD'. These characteristics in combination distinguish 'IFALCOD' as a new and distinct *Allium* plant:

1. Upright plant habit with upright flowering stems.
2. Moderately vigorous to vigorous growth habit and moderately rapid growth rate.
3. Ensiform medium green-colored leaves.
4. Early and freely flowering habit.
5. Numerous white-colored flowers arranged on dense inflorescences.
6. Long flowering period.
7. Good garden performance.

Plants of the new *Allium* differ primarily from plants of the female parent selection in the following characteristics:

1. Plants of the new *Allium* are more compact than plants of the female parent selection.
2. Plants of the new *Allium* are more freely flowering than plants of the female parent selection.

Plants of the new *Allium* can be compared to plants of *Allium hybrida* 'Milennium', not patented. Plants of the new *Allium* differ primarily from plants of 'Milennium' in flower color as plants of the new *Allium* have white-colored flowers whereas plants of 'Millennium' have purple-colored flowers.

BRIEF DESCRIPTION OF THE PHOTOGRAPHS

The accompanying colored photographs illustrate the overall appearance of the new *Allium* plant showing the colors as true as it is reasonably possible to obtain in colored reproductions of this type. Colors in the photographs may differ slightly from the color values cited in the detailed botanical description which accurately describe the colors of the new *Allium* plant.

The photograph on the first sheet (FIG. 1) is a side perspective view of typical flowering plant of 'IFALCOD' grown in a container.

Figure 2:
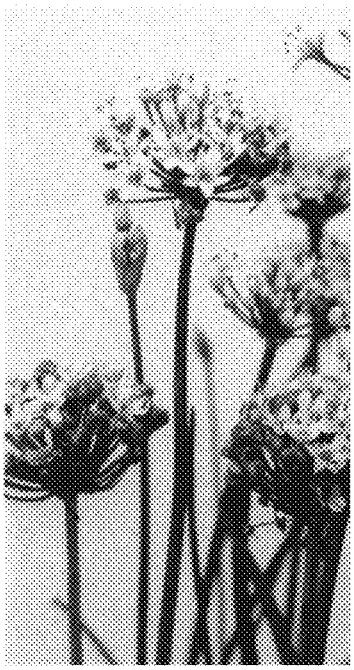

The photograph on the left side of the second sheet (FIG. 2) is a close-up view of typical inflorescences of 'IFALCOD'.

Figure 3:
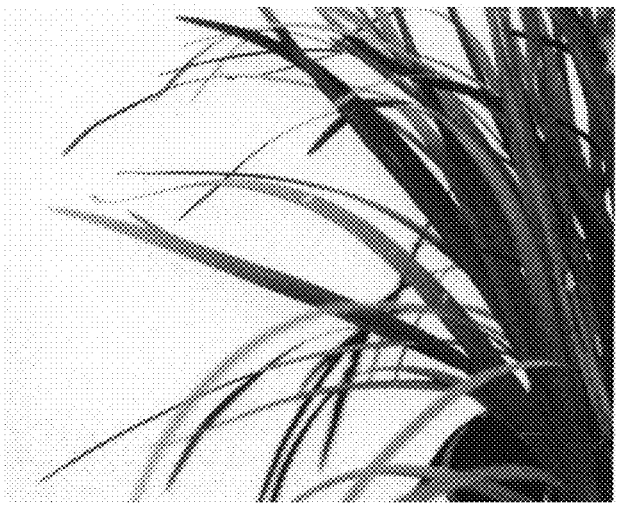

The photograph on the right side of the second sheet (FIG. 3) is a close-up view of typical leaves of 'IFALCOD'.

DETAILED BOTANICAL DESCRIPTION

The aforementioned photographs and following observations, measurements and values describe plants grown during the late summer in 15-cm containers in an outdoor nursery in Heerhugowaard, The Netherlands and under cultural practices typical of commercial *Allium* production. During the production of the plants, day temperatures ranged from 15° C. to 30° C. and night temperatures ranged from 8° C. to 20° C. Plants were five months old when the photographs and description were taken. In the following description, color references are made to The Royal Horticultural Society Colour Chart, 2015 Edition, except where general terms of ordinary dictionary significance are used.

Botanical classification: *Allium tuberosum* 'IFALCOD'.

Parentage:

- *Female, or seed, parent.*—Unnamed selection of *Allium tuberosum*, not patented.
- *Male, or pollen, parent.*—Unknown selection of *Allium tuberosum*, not patented.

Propagation:

- *Type.*—By divisions.
- *Time to produce a rooted young plant, summer.*—About three months at temperatures about 18° C.
- *Root description.*—Thick; fleshy; typically white in color, actual color of the roots is dependent on substrate composition, water quality, fertilizer type and formulation, substrate temperature and physiological age of roots.
- *Rooting habit.*—Moderately freely branching; sparse.
- *Bulbs.*—To date, bulb development has not been observed on plants of the new *Allium*.

Plant description:

- *Plant and growth habit.*—Herbaceous perennial typically grown as a garden plant; upright plant habit, overall plant shape, broadly ovate; moderately vigorous to vigorous growth habit and moderate growth rate; globular basal rosette of leaves with upright flowering stems.
- *Plant height, soil level to top of foliar plane.*—About 27.3 cm.
- *Plant height, soil level to top of floral plane.*—About 38.5 cm.
- *Plant width* (*spread*).—About 43.5 cm.

Leaf description:

- *Arrangement.*—Leaves are arranged in basal rosettes with about five to seven leaves per rosette; leaves sheathing and sessile.
- *Length.*—About 25.6 cm.
- *Width.*—About 5 mm to 9 mm.
- *Shape.*—Ensiform; blade is mostly flat.
- *Apex.*—Acute.
- *Base.*—Sheathing.
- *Margin.*—Entire, not undulate.
- *Texture and luster, upper and lower surfaces.*—Smooth, glabrous; slightly glossy.
- *Venation pattern.*—Parallel.
- *Color.*—Developing leaves, upper surface: Close to 143A. Developing leaves, lower surface: Close to between 143B and 144A. Fully developed leaves, upper surface: Close to between 137B and 143A; venation, close to between 137B and 143A. Fully developed leaves, lower surface: Close to 137B; venation, close to 143A.
- *Leaf sheaths.*—Length: About 1.5 cm. Diameter: About 3 mm. Texture and luster, upper and lower surfaces: Smooth, glabrous; slightly glossy. Color, upper and lower surfaces: Close to 157C to 157D.

Flower description:

- *Flower type, arrangement and habit.*—Single rotate flowers arranged on umbels; umbels flattened globular in shape; freely flowering habit with about 55 flowers developing per inflorescence and about 1,200 flowers per plant; flowers face upright to outwardly depending on position on the umbel.
- *Natural flowering season.*—Plants flower from July into September in The Netherlands; plants begin flowering about four months after planting rooted young plants.
- *Flower longevity on the plant.*—Individual flowers last about 3.5 weeks on the plant; flowers persistent.
- *Fragrance.*—Faint; sweet and pleasant, onion-like.
- *Flower buds.*—Length: About 6 mm. Diameter: About 3.5 mm. Shape: Oblong. Texture and luster: Smooth, glabrous; slightly glossy. Color: Close to NN155C; main veins, close to 177B.
- *Inflorescence height.*—About 3.1 cm.
- *Inflorescence diameter.*—About 4.9 cm.
- *Flower diameter.*—About 1.2 cm by 1.2 cm.
- *Flower depth.*—About 6 mm.
- *Tepals.*—Quantity and arrangement: Six arranged in two whorls. Upper whorl of tepals: Length: About 6 mm. Width: About 3 mm. Shape: Ovate to broadly ovate, concave. Apex: Broadly and bluntly acute. Base: Broadly cuneate. Margin: Entire, not undulate. Texture and luster, upper and lower surfaces: Smooth, glabrous; slightly glossy. Color: When opening, upper surface: Close to NN155D. When opening, lower surface: Close to NN155B. Fully opened, upper surface: Close to NN155D; venation, close to NN155D; color does not change with subsequent development. Fully opened, lower surface: Close to NN155B; venation, close to 177C and distally, close to 177D; color does not change with subsequent development. Lower whorl of tepals: Length: About 6 mm. Width: About 2.25 mm. Shape: Ovate to broadly ovate, concave. Apex: Acute. Base: Broadly cuneate. Margin: Entire, not undulate. Texture and luster, upper and lower surfaces: Smooth, glabrous; slightly glossy. Color: When opening, upper surface: Close to NN155D. When opening, lower surface: Close to NN155B. Fully opened, upper surface: Close to NN155D; venation, close to NN155D; color does not change with subsequent development. Fully opened, lower surface: Close to NN155B; venation, close to 144C and distally, close to 177B; color does not change with subsequent development.

*Scapes.*—Length: About 30.1 cm. Diameter: About 4 mm by 7 mm. Aspect: Erect to about 15° from vertical. Strength: Strong. Texture and luster: Smooth, glabrous; glaucous. Color: Close to 137A; waxy layer, close to 191A.

*Pedicels.*—Length: About 1.9 cm. Diameter: About 1 mm. Aspect: Erect to horizontal depending on position on umbel. Strength: Strong. Texture and luster: Smooth, glabrous; moderately glossy. Color: Close to 143B.

*Inflorescence bracts.*—Arrangement: Subtending the tepals and bi-parted. Length: About 1.6 cm. Width: About 1 cm. Texture: Papery. Color: Close to 150D; venation, close to 144C and becoming closer to 162A with development.

*Reproductive organs.*—Stamens: Quantity per flower: Six. Filament length: About 4 mm. Filament color: Close to NN155C. Anther shape: Basifixed, oblong. Anther size: About 1 mm by 2 mm. Anther color: Close to N167C. Pollen amount: Scarce. Pollen color: Close to 12A. Pistils: Quantity per flower: One. Pistil length: About 3 mm. Style length: About 3 mm. Style color: Close to NN155D. Stigma size: About 0.2 mm by 0.5 mm. Stigma shape: Pointed. Stigma color: Close to NN155D. Ovary color: Close to between 147A and N189B.

*Seeds and fruits.*—To date, seed and fruit production have not been observed on plants of the new *Allium.*

Pathogen & pest resistance: To date, plants of the new *Allium* have not been observed to be resistant to pathogens and pests common to *Allium* plants.

Garden performance: Plants of the new *Allium* have exhibited good tolerance to rain, wind and temperatures ranging from about −23° C. to about 40° C. and to be suitable for USDA Hardiness Zones 5 to 10.

It is claimed:

1. A new and distinct *Allium* plant named 'IFALCOD' as illustrated and described.

* * * * *